United States Patent
Guidry et al.

(10) Patent No.: US 10,130,505 B2
(45) Date of Patent: Nov. 20, 2018

(54) OSTOMY POUCH REPLACEMENT DEVICE

(71) Applicants: Liney Guidry, Baton Rouge, LA (US);
Theresa Johnson, Simpsonville, SC (US); Reed Johnson, Cumming, GA (US); Bruce Johnson, Simpsonville, SC (US)

(72) Inventors: Liney Guidry, Baton Rouge, LA (US); Theresa Johnson, Simpsonville, SC (US); Reed Johnson, Cumming, GA (US); Bruce Johnson, Simpsonville, SC (US)

( * ) Notice: Subject to any disclaimer, the term of this patent is extended or adjusted under 35 U.S.C. 154(b) by 457 days.

(21) Appl. No.: 14/960,759

(22) Filed: Dec. 7, 2015

(65) Prior Publication Data

US 2017/0156917 A1   Jun. 8, 2017

(51) Int. Cl.
*A61F 5/44* (2006.01)
*A61F 5/448* (2006.01)
*A61F 5/443* (2006.01)

(52) U.S. Cl.
CPC .......... *A61F 5/4404* (2013.01); *A61F 5/4401* (2013.01); *A61F 5/443* (2013.01); *A61F 5/448* (2013.01); *A61F 2005/4402* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,520,301 A | * | 7/1970 | Leonard | A61F 5/448 604/338 |
| 4,187,850 A | * | 2/1980 | Gust | A61F 5/445 604/338 |
| 4,344,433 A | * | 8/1982 | Smith | A61F 5/445 604/344 |
| 4,344,435 A | | 8/1982 | Aubin | |
| 4,686,355 A | * | 8/1987 | Lay | A61F 5/445 108/33 |
| 4,726,354 A | * | 2/1988 | Fujita | A61F 5/445 600/32 |

(Continued)

FOREIGN PATENT DOCUMENTS

CN   204106295U-1   1/2015

*Primary Examiner* — Tatyana Zalukaeva
*Assistant Examiner* — Guy K Townsend
(74) *Attorney, Agent, or Firm* — Southeast IP Group, LLC; Thomas L. Moses (57) ABSTRACT

An ostomy pouch replacement device is provided to allow ostomates with a surgically created stoma to collect, contain and dispose of bodily fluids during frequent hygienic maintenance. The device is customizable to each ostomate's unique stoma diameter and provides a disposable waste receptacle designed to have a hollow absorbent section and a solid absorbent section for sanitary, discreet and odorless disposal of both urine and excrement. The device preferably consists of a disposable waste receptacle that may be positioned over the stoma and further includes an absorbent inner material for capturing any waste that may be discharged, a push cap for pressing the absorbent material to the stoma, a cap or plug for sealing the device after use, and a collar stand for pressing an adhesive wafer to the skin and for holding the assembled device in an upright position.

11 Claims, 7 Drawing Sheets

(56) References Cited

U.S. PATENT DOCUMENTS

| | | | |
|---|---|---|---|
| 4,850,986 A * | 7/1989 | Temple | A61F 5/44 604/355 |
| 5,125,916 A | 6/1992 | Panebianco et al. | |
| 5,312,384 A * | 5/1994 | Temple | A61F 5/44 604/355 |
| 5,421,827 A * | 6/1995 | Temple | A61F 5/451 383/67 |
| 6,186,990 B1 * | 2/2001 | Chen | A61F 5/44 4/451 |
| 6,409,709 B1 * | 6/2002 | Recto | A61F 5/445 604/327 |
| 6,579,271 B1 * | 6/2003 | Aruffo | A61F 17/00 206/440 |
| 6,916,312 B2 * | 7/2005 | Kondo | A61F 5/443 604/277 |
| 6,929,627 B2 * | 8/2005 | Mahoney | A61F 5/445 604/332 |
| 2003/0040727 A1 * | 2/2003 | Boulanger | A61F 5/445 604/332 |
| 2012/0123379 A1 | 5/2012 | Forsell | |
| 2012/0277700 A1 * | 11/2012 | Amer, Jr. | A61F 5/445 604/332 |
| 2017/0156917 A1 * | 6/2017 | Guidry | A61F 5/4404 |
| 2018/0028347 A1 * | 2/2018 | Guidry | A61F 5/4404 |

* cited by examiner

OSTOMY POUCH REPLACEMENT DEVICE

BACKGROUND OF THE INVENTION

The present invention relates to a personal care apparatus and, in particular, to an apparatus for collecting, containing and disposing of waste matter, during the replacement of a stoma bag for those people having had surgical operations for removing a bladder or colon.

Surgical procedures such as colostomies, cystostomies, urostomies and ileostomies involve rerouting of the colon or ureter so that waste materials can be discharged through an artificial opening formed in the ostomy patient's (also referred to herein as ostomate) body. This artificial opening, called a stoma, is typically located in the abdomen and may be about 0.5 to 1.0 inch or more in diameter. A stoma is connected directly to the kidney by a rerouted ureter or to the intestines by the rerouted colon and the discharge of waste matter in each instance is made through the stoma.

The new artificial opening, or stoma, made on the abdominal wall, has no voluntary sphincter control by the ostomate. Collection of involuntary waste seepage is by bag or other receptacle attached to the ostomate's body. Disposable and semi-disposable bags for such purposes are available from several commercial sources. The disposable bags come as assembled units which are applied to the body. Such bags are attached to the body over the stoma by means of a ring-like member known as a wafer or face plate and a sealing ring of double sided adhesive which must be assembled and positioned over the stoma with precision to achieve a reliable attachment and seal. It is essential that this ring be mounted directly and concentrically over the stoma and further, that it be tightly secured to the body, otherwise leakage of waste onto the surrounding skin area can occur. After removal of the filled bag, the common practice in the past has been to first clean and dry the stoma and surrounding skin area before application of the sealing ring to the skin, followed by connection of the face plate to the sealing ring and then attachment of a new bag to the face plate. It is most important that the skin area surrounding the stoma be kept clean and dry during replacement of the bag to avoid infection and to achieve a good connection between the skin, sealing ring and face plate. Adhesive tape is sometimes applied over the edges of the face plate and sealing ring for extra reinforcement. Inadvertent disconnection of a bag can cause considerable inconvenience and embarrassment to an ostomate.

In the replacement of the ostomy appliance, the general procedure is first to remove the ring and the receptacle. The ostomate applies an absorbent material of choice on top of the stoma to absorb any waste matter and prevent it from leaking onto the surrounding skin prior to the application of the adhesive. The surrounding skin must be cleaned and dried. This is generally accomplished by the use of a commercially available "prep" agent, which removes the skin oils, cleans the skin, and leaves a dry skin surface. Upon application of the adhesive, the absorbent material is removed from the stoma and a wafer or ring is placed over the stoma in a precisely centered position. Generally, one must remain in a standing position and using a mirror to achieve the centered position. The ostomy appliance is then attached to the ring and tightly secured to the skin.

Several patents and publications describe devices designed to assist ostomates in the replacement of an ostomy device, including the following patents incorporated herein by reference.

U.S. Pat. No. 6,409,709 describes an ostomy-changing facilitating device for absorbing fluids from the stoma during the change of the more permanent ostomy appliance. The ostomy-changing facilitating device includes a tubular member with absorbent material filling the bore of the tubular member.

U.S. Pat. No. 8,343,119 describes a cap device for home use to temporarily cover the stoma resulting from a urostomy, colostomy or ileostomy procedure. It provides a means of preventing leakage during routine cleaning around the stoma during the ostomy pouch replacement process.

U.S. Pat. No. 4,187,850 describes a medical-surgical method and apparatus for facilitating the replacement of ostomy appliances. A hollow cylinder, filled with sterile absorbent material is used to center the sealing ring prior to the replacement of the ostomy appliance.

U.S. Pat. No. 4,344,433 describes an appliance for facilitating replacement of a waste bag by an ostomy patient comprising a base, an upright post removeably seated in said base, and a slideable collar supported on an abuttment on said post. One end of the post includes an opening which covers the stoma and collects any seepage during the replacement procedure. This particular device requires that the face plate and adhesive sealing ring be preassembled on the post and collar, after which the post is removed from the base and positioned over the stoma.

The aforementioned prior art do not include all the features and advantages of the present invention, more specifically, the present device provides an absorbent waste receptacle with a dual absorbency chamber designed to effectively collect, contain and dispose of both urine and excrement; whereas the prior art typically provides only a hollow chamber, or a chamber entirely packed with absorbent material. The device of the present invention does not require preassembly of an ostomy appliance (such as pouch and wafer) or preassembly of the device itself, therefore allowing an ostomate to take ample time to prepare and perform the pouch replacement process. Furthermore, the device of the present invention provides an absorbent waste receptacle that is customizable to a particular ostomate's stoma as well as being disposable for a sanitary and discreet disposal of waste.

BRIEF SUMMARY OF THE INVENTION

The present invention relates to an ostomy pouch replacement device that allows ostomates with a surgically created stoma to collect, contain and dispose of waste matter during frequent hygienic maintenance. In a preferred embodiment, the device consists of multiple pieces and sections, such as an optional alignment sleeve, a disposable waste receptacle, a cap or plug, a push cap, and a collar stand.

One aspect of the present invention is to provide a device that is customizable to each ostomate's unique stoma diameter and provides a disposable waste receptacle for a sanitary, discreet and odorless disposal of waste. The present device can be used by a broad range of ostomates due to the dual absorbency chamber of the waste receptacle. The receptacle is preferably designed to have a hollow absorbent section and a solid absorbent section to allow for the collection, containment and disposal of both urine and excrement for use in colostomies, ileostomies, and urostomies.

Another aspect of the present invention is to provide a device that can be used during pouch replacement to provide an ostomate ample time to clean and prep the skin area surrounding the stoma, prior to attaching a clean adhesive barrier member and pouch.

DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
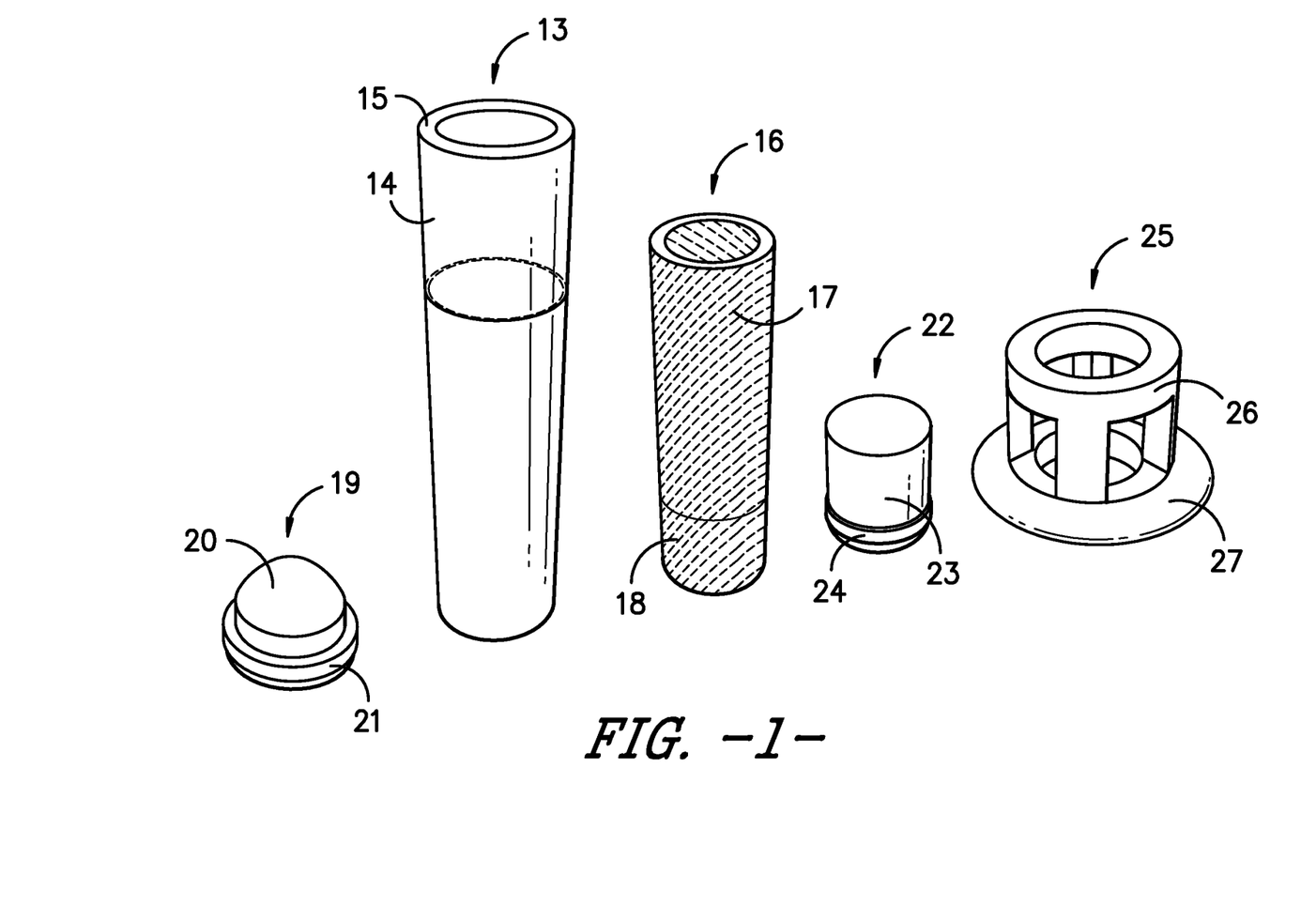
FIG. 1 illustrates an embodiment of the present invention whereby the apparatus is disassembled so that each component may be viewed separately.

FIG. 1 illustrates an embodiment of the present invention in a disassembled form. The device preferably consists of a disposable waste receptacle 13 for positioning the device over the stoma and for capturing any waste that may be discharged, a cap or plug 19 for sealing the device after use, a push cap 22 for pressing or pushing an absorbent member 16 within the waste receptacle 13 and against the stoma, and a collar stand 25 for sealing an adhesive wafer to the skin and for holding the assembled device in an upright position. The device may also consist of a reusable alignment sleeve to aid in positioning the waste receptacle 13 over the stoma.

The waste receptacle 13 is preferably a hollow cylindrical-shaped tube, open on both ends, and adapted to receive an absorbent member 16. One end of the tube is for positioning over a stoma (referred to herein as the "proximal end" or "stoma end"), the opposite end (or "distal end") is for insertion of the absorbent member (see FIGS. 2 and 3a-b). The diameter and dimensions of the tube may be customizable depending on the shape and diameter of the stoma over which the tube is designed to fit; however, preferred dimensions are approximately 5-7 inches in length with an inner diameter sufficient to entirely surround the stoma. In a preferred embodiment, at least a portion of the proximal end 14 of the waste receptacle 13 is transparent for easily positioning and centering the receptacle 13 directly over an ostomate's stoma. This stoma end 14 also may be rounded off or include a smooth ring 15 that fits flush over the end of the receptacle 13. This ring 15 provides a more comfortable fit against an ostomate's skin, as well as forming a small inner lip at the end of the sleeve 13 for fitting flush against the absorbent member 16 once the member 16 is fully pressed against the stoma (see FIG. 3b). The waste receptacle 13 may be constructed of materials such as cardboard, paper, plastic, polystyrene foam, or any other suitable disposable material. The waste receptacle 13 may also be designed from biodegradable materials such as bioplastic with an organic cotton inner lining and absorbent section.

Figure 2:
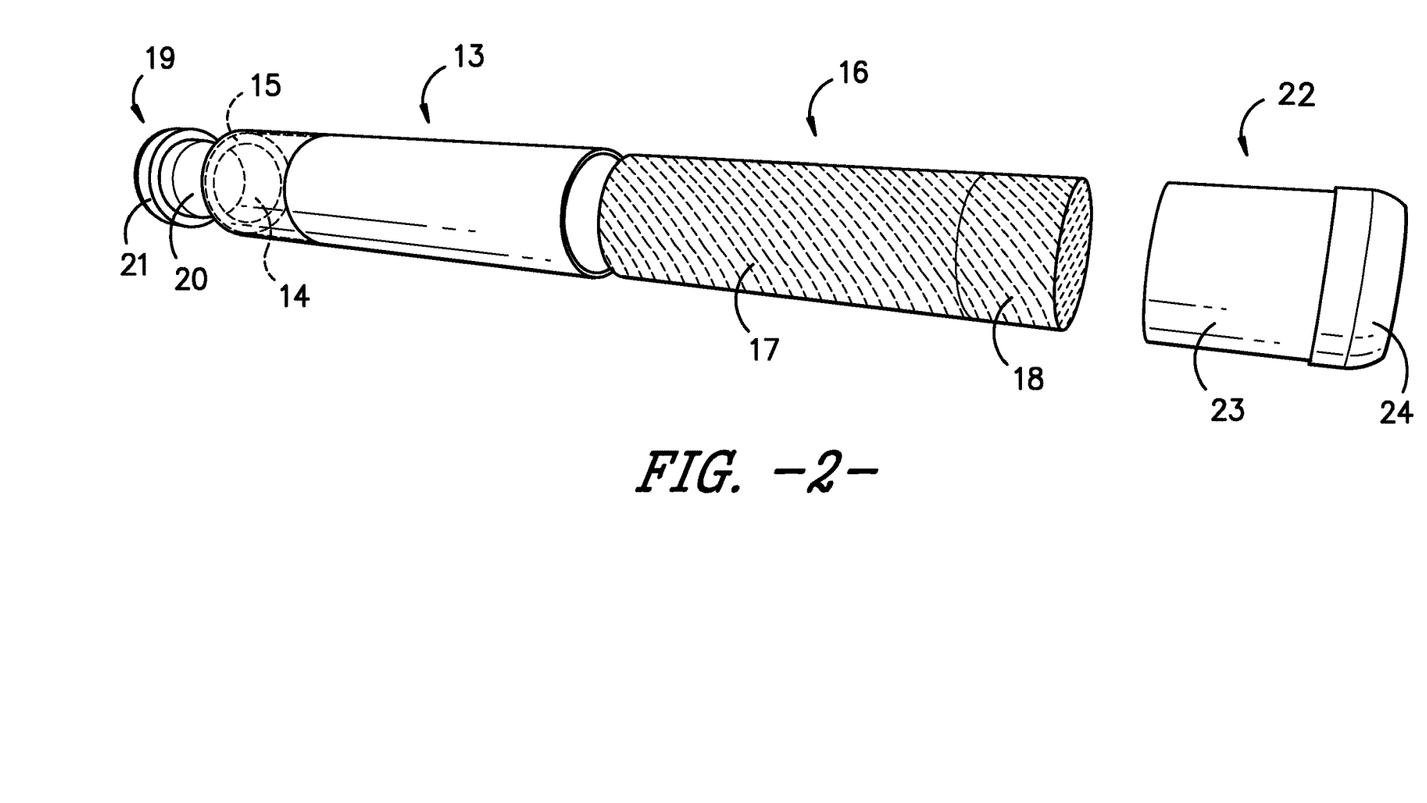
FIG. 2 illustrates an exploded view of one embodiment of an ostomy pouch replacement device.
Figure 3A:
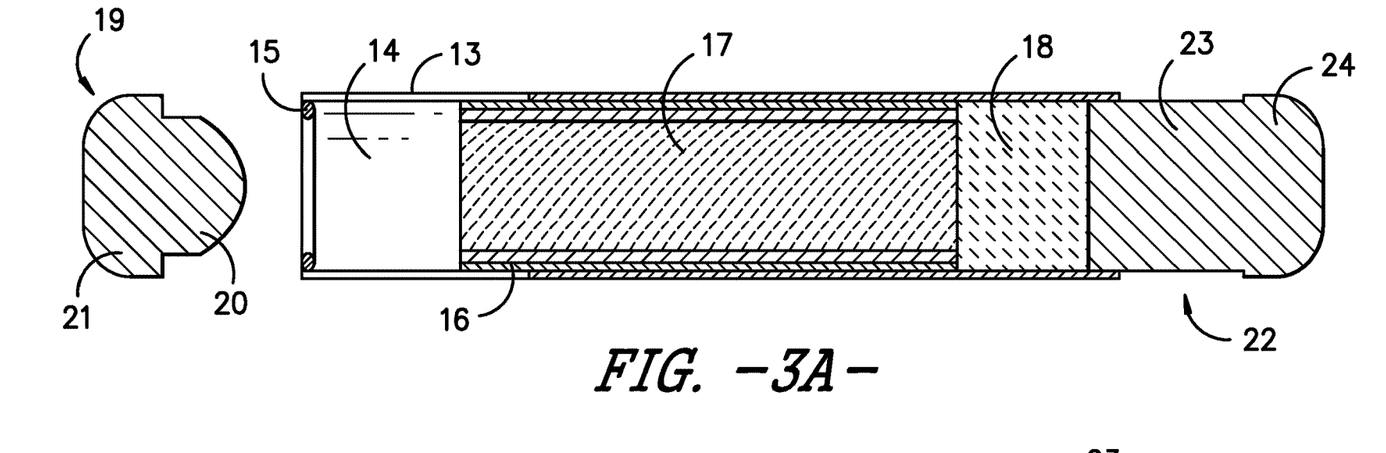
FIG. 3A represents a cross-sectional view of one embodiment of an ostomy pouch replacement device illustrating the absorbent member being inserted into the waste receptacle through use of a push cap.
Figure 3B:
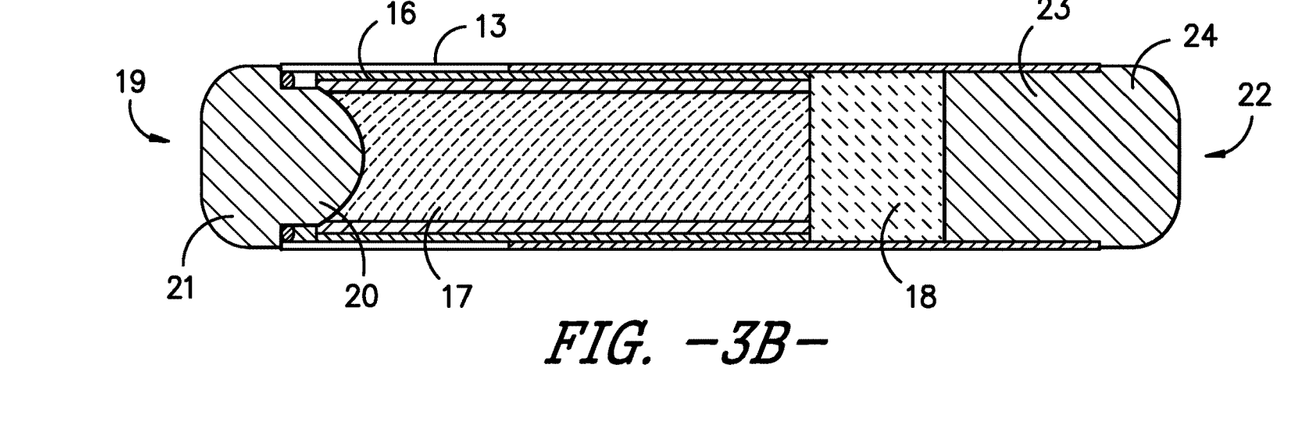
FIG. 3B represents a cross-sectional view of one embodiment of an ostomy pouch replacement device illustrating the absorbent member fully inserted into the waste receptacle and capped off at the proximal end.
Figure 4:
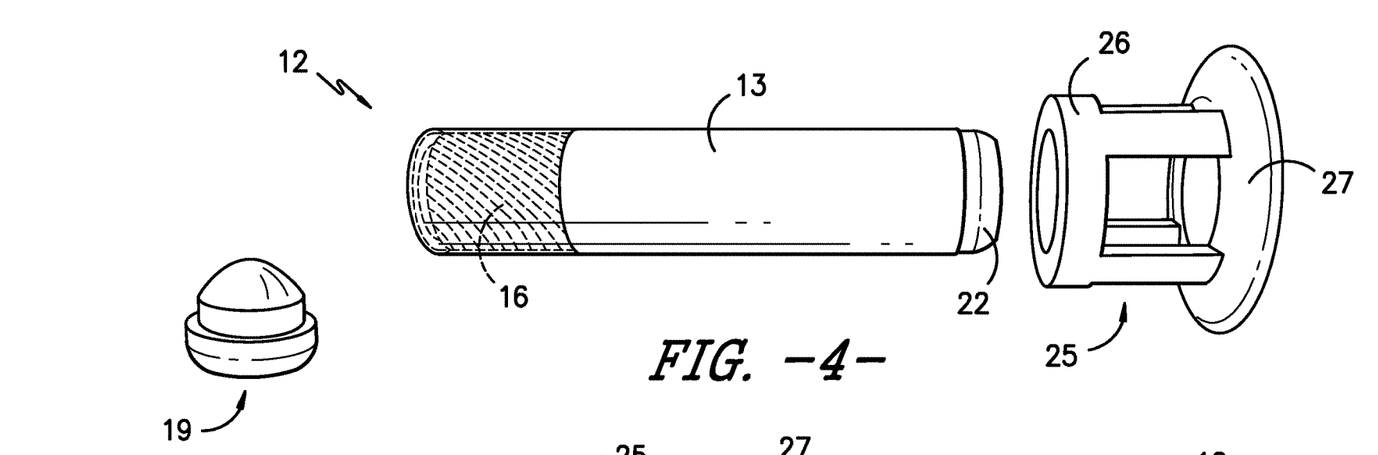
FIG. 4 illustrates an earlier step in the pouch replacement process whereby the device is aligned and positioned over the stoma, and the collar stand is positioned to slide over the device.

In one embodiment, the absorbent member 16 (also referred to herein as "absorbent tube") is disposable and may be a cylindrical-shaped tube, preferably open on one end ("proximal end") with the opposite or distal end being sealed or closed off. The open end may be inserted into the waste receptacle 13 (as shown in FIGS. 2 and 3a-b) and positioned against the stoma for receiving waste that may be involuntarily discharged from the stoma during pouch replacement. The waste material may be received by a hollow portion 17 of the absorbent tube 16, this portion 17 preferably having an absorbent and/or wicking material lining the inner surface. The remaining length 18 of the absorbent member 16 preferably consists of a dense, compacted absorbent and/or wicking material abutting the sealed end of the receptacle 13, as shown best in FIGS. 3a and 3b. This dense absorbent section 18 could be constructed of compacted fibers, beads, pellets, or any other suitable material. By providing both a hollow absorbent section 17 and compacted absorbent section 18, the waste receptacle 13 with absorbent member 16 is capable of effectively absorbing and retaining both urine and excrement.

The dimensions of the absorbent member 16 may vary and are dependent upon the dimensions of the waste receptacle 13 and the size of the stoma. Specifically, the outer diameter of the absorbent member 16 is preferably less than the inner diameter of the waste receptacle 13, such that the absorbent member 16 may slide inside the receptacle 13 in telescopic fashion, yet fit snugly enough so that all waste material is directed inside the absorbent tube 16 without seepage between the tube 16 and the receptacle 13. The length of the absorbent member 16 is preferably less than the length of the receptacle 13, so that the absorbent tube 16 may be fully inserted into the receptacle 13 and secured in place by the push cap 22. The length of the device may vary as desired; however, it is to be noted that when determining the appropriate length for both the waste receptacle 13 and the absorbent member 16, a greater length will provide a larger capacity for waste containment.

Examples of absorbent material include but are not limited to cotton, rayon, polyester, polyethylene, polypropylene, other suitable fibers, pellets, beads, and combinations thereof. The thickness of both the absorbent lining 17 and dense absorbent section 18 may vary as desired, provided the waste is absorbed as necessary. It is contemplated that the absorbent tube 16 may be offered in a variety of absorbencies so that an ostomate may choose which is best for his or her particular needs. For example, an ostomate with a urostomy may need a tube with maximum absorbency for collecting more urine; whereas an ostomate with a colostomy may need less absorbency, but a longer hollow section 17 for collecting more excrement.

An optional alignment sleeve may also be provided for aiding in the positioning of the device over a stoma. The sleeve is preferably a hollow cylindrical-shaped tube, open on both ends, and adapted to receive a waste receptacle 13. The dimensions of the alignment sleeve may vary and are dependent upon the dimensions of the waste receptacle 13 and the size of the stoma. The diameter of the optional alignment sleeve is preferably greater than the outer diameter of the waste receptacle 13, such that the receptacle 13 may easily, yet snugly, slide inside the sleeve in telescopic fashion. The alignment sleeve may be constructed of materials such as plastic, polyurethane, polycarbonate, silicone rubber, or any other suitable material.

After inserting the absorbent member 16 into the receptacle, the push cap 22 may be used to drive the member 16 further inside the receptacle 13 so that the absorbent material may come in contact with the stoma. A push cap 22 or plunger cap may be used to press the absorbent member 16 to the stoma and serves to cap off the distal end of the device. In a preferred embodiment, the push cap 22 is shaped to have a plunger section 23 that generally corresponds to the inside diameter of the waste receptacle 13 and may be inserted into the waste receptacle 13, and a cap section 24 that is dimensioned such that it seals the distal end of the device and prevents any further insertion of the push cap 22 into the receptacle. The length of the push cap 22 is preferably sufficient to secure the absorbent member 16 inside the waste receptacle 13 and against the stoma. A preferred embodiment of the push cap 22 is shown in FIGS. 2, 3a, and 3b.

A plug 19 is preferably included to seal the proximal, or stoma, end 14 of the device after use. In one embodiment, the plug 19 is dimensioned to correspond in diameter to the push cap 22 in order to fit snugly and securely within the waste receptacle 13. The plug 19 preferably includes a first portion 20 that fits within the waste receptacle 13, fully sealing the receptacle 13 so that all waste is contained. A second portion 21 of the plug 19 preferably has a larger diameter than the first portion 20, for capping off or fully sealing the proximal end 14 of the waste receptacle 13, as shown in FIG. 3b. The length of the first portion 20 of the plug 19 should be such that the plug 19 fits deeply enough into the waste receptacle 13 to prevent seepage out of the tube, but not so deep that the plug is displacing any waste that may be present in the tube. The plug 19 is preferably constructed of a material such as plastic, polyurethane, polycarbonate, or any other suitable disposable material.

Figure 5:
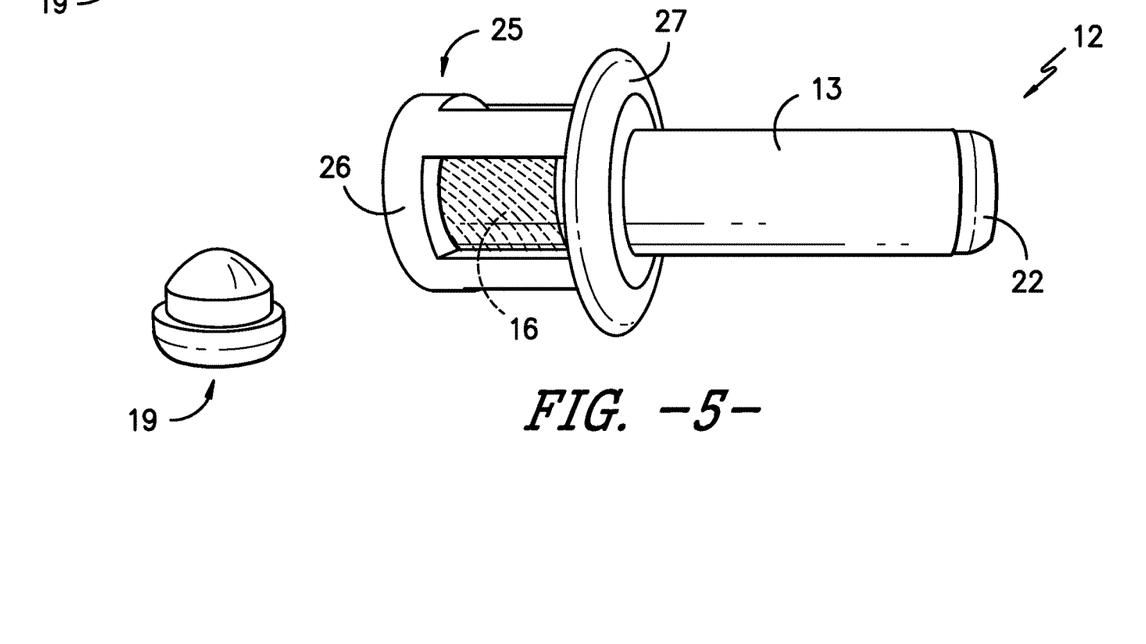
FIG. 5 illustrates a step in the pouch replacement process whereby the collar stand of the device would be pressed firmly against the stoma, thereby sealing an adhesive skin barrier to skin.
Figure 8:
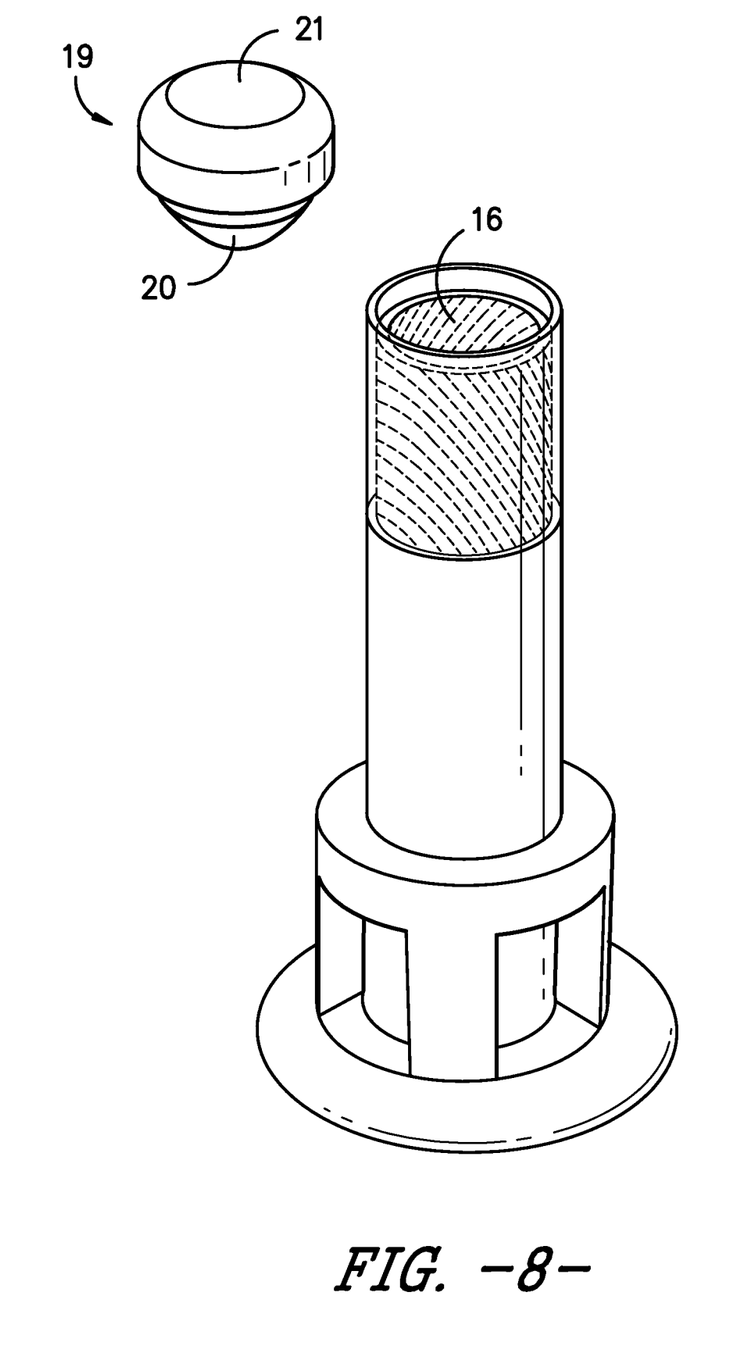
FIG. 8 illustrates a step in the pouch replacement process whereby the device is capped off and ready for disposal of the waste receptacle.
Figure 9:
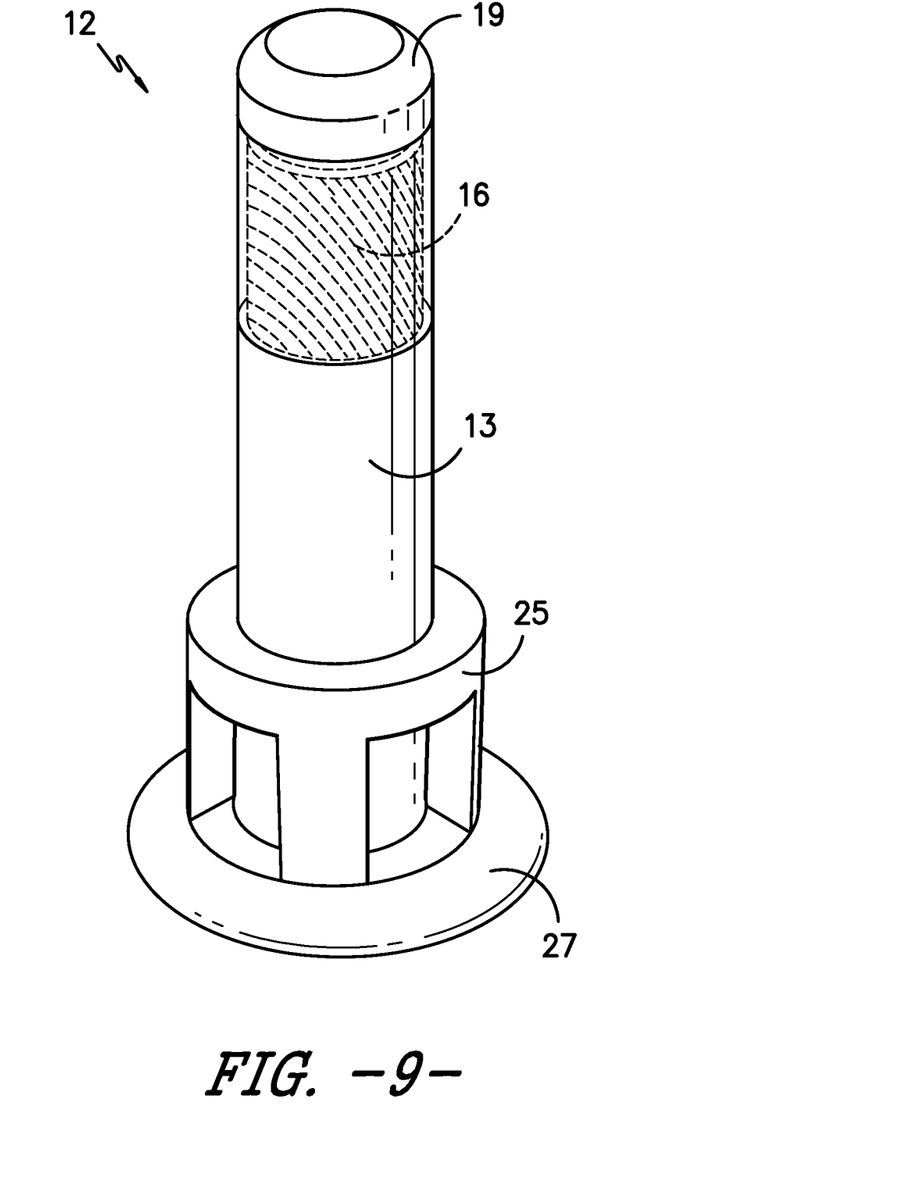
FIG. 9 illustrates a step in the pouch replacement process whereby the used device is placed upright in the collar stand to hold the device in place and prevent spillage.

A collar stand 25 may be provided to aid the application of a skin barrier member such as an adhesive wafer, ring, or face plate, during the pouch replacement process, as shown in FIG. 5. Furthermore, the collar 25 may act as a stand in which the assembled device 12 can be placed and held in an upright position, as shown in FIGS. 8 and 9. In one embodiment, the collar stand 25 consists of an open-ended cylindrical section 26 with a flange 27 on one end for providing support and stability in an upright position. The cylindrical section 26 has an inner diameter large enough to freely and easily slide the collar 25 back and forth along the full length of the waste receptacle 13, and a thickness sufficient to distribute equal and adequate force when pressing an adhesive wafer or face plate against the skin. The collar stand 25 may be constructed of any suitable material such as plastic, polyurethane, polycarbonate, silicone rubber, or stainless steel.

Figure 6:
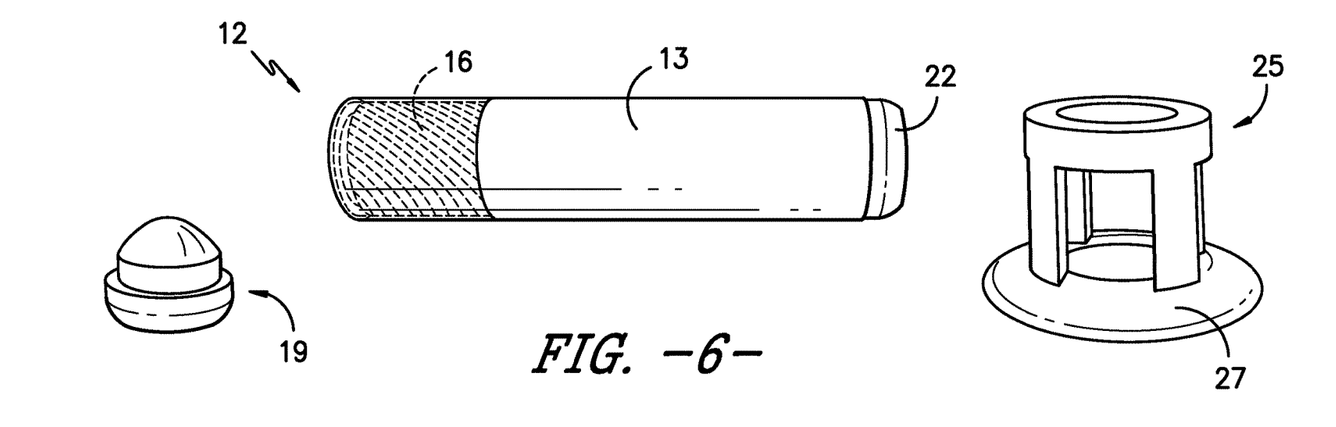
FIG. 6 illustrates a step is the pouch replacement process whereby the collar stand has been removed from the device and is positioned for use as a stand.
Figure 7:
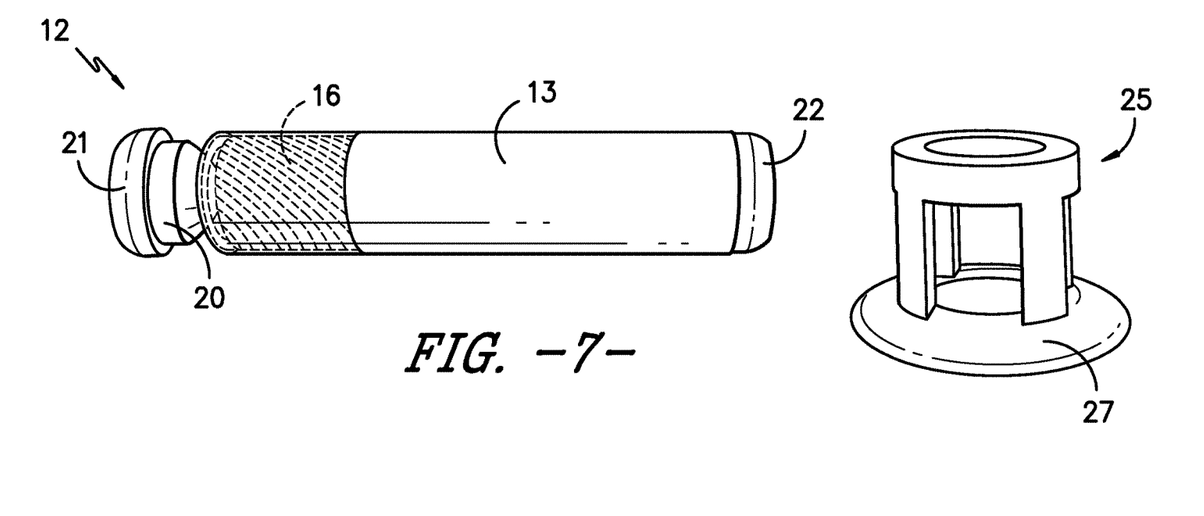
FIG. 7 illustrates a step in the replacement process whereby the device has been removed from the stoma and is being capped off to retain any waste contents within the waste receptacle.

The ostomy pouch replacement device of the present invention may have many uses, an exemplary use being described herein. It is contemplated that the device of the present invention may be provided to an ostomate with the absorbent member 16 already inserted telescopically into the distal end of the waste receptacle 13, allowing for immediate use without much preassembly. An initial step in replacing an ostomy pouch involves removing a filled or used ostomy pouch from the adhesive barrier member (such as a wafer, sealing ring or face plate), followed by removal of the adhesive barrier member from the skin. At this point in the process, a preferred step is to center the proximal end of the waste receptacle 13 (preceded by the optional alignment sleeve, if so desired) directly over the stoma, using the transparent portion 14 of the receptacle 13 to guide the positioning, as shown in FIG. 2. At this step, the push cap 22 or plunger cap is used to press or drive the absorbent member 16 further inside the receptacle 13, as shown in FIG. 3a, so that the open end of the absorbent tube 16 is flush with the ring 15 at the stoma end of the receptacle, thus making contact with the stoma. The push cap 22 also serves to cap off or seal the distal end of the waste receptacle 13, securing the absorbent member 16 inside the sleeve. Once the waste receptacle 13 is in place, the user can take as much time as necessary to clean and prep the skin around the stoma for application of a new skin barrier member and clean pouch. Any waste matter that may involuntarily discharge at this time is captured and contained within the waste receptacle 13. Once the skin is prepped and a new adhesive barrier member is ready to be applied, the barrier member is cut to match a diameter that best fits around the stoma and is placed over the distal end of the device followed by the collar stand 25. The collar assists in sliding the wafer toward the stoma, as shown by FIG. 5, thus providing even pressure to press the wafer against the skin, ensuring tight adhesion and a good seal on the skin. Once the adhesive barrier member is applied, the collar 25 is removed and placed in an upright position, as illustrated in FIG. 6. The used device is removed or pulled away from the stoma, as shown in FIGS. 7 and 8. The waste receptacle 13 is either sealed at the proximal or stoma end 14 with the plug 19 and place in the stand as in FIG. 9, or alternatively placed in an upright position in the collar stand 25, as in FIG. 8, and then sealed with plug 19 to avoid any spillage of waste while allowing for free hands to attach a new pouch to the wafer or face plate. At this point in the process both ends of the waste receptacle 13 are sealed, effectively securing and containing any and all waste inside the device. Once pouch replacement is complete, the disposable waste receptacle 13 is removed from the reusable collar stand 25 and safely discarded.

Although the ostomy pouch replacement device of the present invention has been described in detail with reference to particular embodiments and dimensions, the embodiments are for illustrative purposes only and do not limit the invention. It is to be appreciated that those skilled in the art can change or modify the embodiments without departing from the scope and spirit of the invention. It is to be understood that the inventive concept is not to be considered limited to the constructions and dimensions disclosed herein.

The terms used in the present application are merely used to describe particular embodiments, and are not intended to limit the present invention. An expression used in the singular encompasses the expression of the plural, unless it has a clearly different meaning in the context. In the present application, it is to be understood that the terms such as "including" or "having." etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

What is claimed is:

1. An ostomy pouch replacement device comprising:
   a receptacle in the form of a cylindrical tube having an open proximal end dimensioned for placement over and surrounding a stoma and adapted to receive an inner absorbent member, said receptacle having a closed distal end, an open proximal end, an inner diameter, an outer diameter;
   an inner absorbent member adapted for receiving stoma effluent and in the form of a cylindrical shape having an outer diameter dimensioned and adapted to slidably insert into said cylindrical-shaped receptacle, said inner absorbent member having an open proximal end, a closed distal end, an inner diameter, and said outer diameter of said cylindrical-shaped absorbent member is less than said inner diameter of said cylindrical-shaped tube of said receptacle;
   a plug member adapted for tight insertion into said proximal end of said receptacle; and
   a collar stand comprising a cylindrical section having a first open end and a second open end, and further including a flange extending outwardly from said first open end that serves as a base member, said collar stand adapted for telescopic movement along an outer surface of said receptacle, wherein said collar stand is used to apply pressure to a skin barrier member, and is further used to hold and support said receptacle in an upright manner on a horizontal surface.

2. The ostomy pouch replacement device of claim 1, whereby said inner absorbent member has hollow inner portion adapted to receive excrement and a substantially solid absorbent portion for absorbing liquid waste discharged from a stoma.

3. The ostomy pouch replacement device of claim 2, whereby a first section of said inner member adjacent said proximal end is hollow, and said inner diameter of said first section is lined with an absorbent material; and
   whereby a second section of said inner member adjacent said distal end is generally filled with an absorbent material.

4. The ostomy pouch replacement device of claim 3, whereby said absorbent material is selected from the group consisting of cotton, rayon, polyester, polyethylene, polypropylene, fibers, pellets, beads, and combinations thereof.

5. The ostomy pouch replacement device of claim 1, whereby said receptacle and said inner absorbent member are disposable.

6. The ostomy pouch replacement device of claim 1, whereby said device is disposable.

7. The ostomy pouch replacement device of claim 1, whereby at least a portion of said receptacle is transparent.

8. An ostomy pouch replacement device comprising:
   a receptacle in the form of a cylindrical-shaped tube having an open proximal end dimensioned for placement over and surrounding a stoma and adapted to receive an inner member;
   an inner member adapted for receiving stoma effluent and dimensioned to slidably insert into said receptacle;
   a plug member adapted for insertion into a proximal end of said inner member; and
   a collar stand comprising a cylindrical section having a first open end and a second open end, and further including a flange extending outwardly from said first open end that serves as a base member, said collar stand adapted for telescopic movement along an outer surface of said receptacle, wherein said collar stand is used to apply pressure to a skin barrier member, and is further used to hold and support said receptacle in an upright manner on a horizontal surface.

9. A method for changing a used ostomy appliance, comprising the steps of:
   providing an ostomy pouch replacement device comprising a receptacle having an open proximal end for placement over a stoma with an inner member inserted into said receptacle for collecting effluent discharged from the stoma, a cap member, and a collar stand comprising a cylindrical section having a first open end and a second open end, said collar stand further including a flange extending outwardly from said first open end that serves as a base member;
   removing the used ostomy appliance from the stoma;
   centering said open proximal end of said receptacle over the stoma so that the stoma is fully surrounded by said open proximal end of said receptacle and is capable of collecting effluent discharged from the stoma;
   cleaning and drying the skin surrounding the receptacle fully surrounding said stoma;
   sliding a skin barrier member over the device;
   sliding the collar member over and along the device such that the skin barrier member is located between the skin and the collar member;
   pressing the skin barrier member to the skin until the skin barrier member is securely adhered to the skin;
   removing the collar stand from the device and placing on a surface in an upright position;
   withdrawing the ostomy pouch replacement device from the stoma;
   capping off the proximal end of the device;
   placing the device in an upright position in the collar stand; and
   attaching a clean pouch to the skin barrier member.

10. The method of claim 9, further including the steps of:
    providing a plunging member;
    using the plunging member to fully insert the inner member inside the receptacle; and
    sealing the distal end of the device with said plunging member.

11. The method of claim 9, further including the steps of:
    discarding the receptacle and inner member after use.

* * * * *